(12) United States Patent
Li et al.

(10) Patent No.: US 12,075,990 B2
(45) Date of Patent: Sep. 3, 2024

(54) BIOPSY ROTARY CUTTING DEVICE

(71) Applicant: ACCU TARGET MEDIPHARMA (SHANGHAI) CO., LTD., Shanghai (CN)

(72) Inventors: Qi Li, Shanghai (CN); Binkai Xu, Shanghai (CN); Jinting Liu, Shanghai (CN); Kaiqiang Chang, Shanghai (CN); Xiangtong Chang, Shanghai (CN)

(73) Assignee: ACCU TARGET MEDIPHARMA (SHANGHAI) CO., LTD., Shanghai (CN)

( * ) Notice: Subject to any disclaimer, the term of this patent is extended or adjusted under 35 U.S.C. 154(b) by 574 days.

(21) Appl. No.: 17/044,218

(22) PCT Filed: Mar. 7, 2019

(86) PCT No.: PCT/CN2019/077261
§ 371 (c)(1),
(2) Date: Sep. 30, 2020

(87) PCT Pub. No.: WO2020/093635
PCT Pub. Date: May 14, 2020

(65) Prior Publication Data
US 2021/0369255 A1    Dec. 2, 2021

(30) Foreign Application Priority Data
Nov. 9, 2018   (CN) .......................... 201811333582.X (51) Int. Cl.
*A61B 10/02*           (2006.01)
(52) U.S. Cl.
CPC ...... *A61B 10/0275* (2013.01); *A61B 10/0283* (2013.01); *A61B 2010/0208* (2013.01)

(58) Field of Classification Search
CPC ............ A61B 10/0275; A61B 10/0283; A61B 10/0233; A61B 10/02; A61B 17/34; A61B 2010/0208; A61B 2010/045
See application file for complete search history.

(56) References Cited

U.S. PATENT DOCUMENTS

| 2008/0140067 A1 | 6/2008 | Vetter et al. | |
| 2010/0152610 A1* | 6/2010 | Parihar .............. | A61B 10/0275 600/566 |
| 2013/0226030 A1* | 8/2013 | McGhie ............. | A61B 10/0275 600/567 |

FOREIGN PATENT DOCUMENTS

| CN | 201139587 Y | 10/2008 |
| CN | 104188693 A | 12/2014 |

(Continued)

OTHER PUBLICATIONS

PCT/CN2019/077261 International Search Report dated Aug. 7, 2019 and English translation.

*Primary Examiner* — May A Abouelela
*Assistant Examiner* — Anna Roberts
(74) *Attorney, Agent, or Firm* — NZ CARR LAW OFFICE (57) ABSTRACT

The present invention provides a biopsy rotary cutting device, which comprises a dynamic sealing structure(4) arranged outside an inner cutting cannula(3); the dynamic sealing structure(4) forms a cavity outside the inner cutting cannula(3); the inner cutting cannula(3) comprises a first tube section(31) and a second tube section(32) that are arranged in sequence along the axial direction of the inner cutting cannula(3); the outer diameter of the second tube section(32) is smaller than that of the first tube section(31); a sealing ring(43) is arranged inside the dynamic sealing structure(4); the cavity comprises a first cavity(41) and a second cavity(42); when the inner cutting cannula(3) moves (Continued)

to a first position along its axial direction, the sealing ring(43) is located at the outer side of the second tube section(32); and there is an inter-cavity gap(46) between the sealing ring(43) and the second tube section(32) to realize communication between the first cavity(41) and the second cavity(42). The present invention can introduce the atmosphere to form a circulating air flow with better suction strength, and the circulating air flow can more efficiently send a rotary-cut tissue at a corresponding position to a sample collector at the back end, thereby effectively improving the sample discharge rate.

20 Claims, 5 Drawing Sheets

(56) References Cited

FOREIGN PATENT DOCUMENTS

| | | |
|---|---|---|
| CN | 104605896 A | 5/2015 |
| CN | 109330632 A | 2/2019 |

\* cited by examiner

BIOPSY ROTARY CUTTING DEVICE

TECHNICAL FIELD

The present invention relates to the field of medical devices, in particular to a biopsy rotary cutting device.

BACKGROUND TECHNIQUE

Biopsy rotary cutting devices are widely used in minimally invasive surgical penetrating operations. First of all, the use of penetrating blades can ensure that the surgical trauma is small and no suturing is needed. It not only can meet the requirements of diagnosis and treatment, but also can ensure a beautiful appearance, especially for breasts or faces, etc., it has the advantages that wounds are small and easily healed, scars left are small, little injury is generated, and quick recovery is achieved, etc., so it is popular with female patient. Nowadays, vacuum-assisted breast sample biopsy and rotary cutting is one of the most effective methods for breast biopsy surgery, suspicious breast lesions need to be repeatedly cut to obtain multiple histological samples of breasts to facilitate early detection and diagnosis of breast cancers and simultaneously realize minimally invasive removal of benign breast tumors.

The distal end of the rotary cutting device implements penetrating with a small-diameter piercer, and the tail of the piercer and the distal end of an outer cutting cannula are fixed coaxially. The outer cutting cannula externally sleeves a coaxially assembled inner cutting cannula. The distal end of the outer cutting cannula has a cutting window; before penetrating is completed, the distal end of the inner cutting cannula is located at the farthest end; after penetrating is completed, the inner cutting cannula rotates backward and the cutting window is opened; and meanwhile tumor tissues are sucked into the cutting window by a vacuum system. The distal end of the inner cutting cannula is provided with an inner chamfered edge; after the tissues are sucked, the inner cutting cannula rotates forward to implement rotary cutting of the tissues; and the cut tissues are sucked into a sample collection container at the tail part of the rotary cutting device via the inner cavity of the inner cutting cannula by continuous vacuum.

The rotary cutting device sucks out the cut tumor tissues mainly through the vacuum system, or it can be understood as that the tissues are conveyed to the sample collection container by pressure difference between the cutting window and the system. However, after the suction resection is completed once, the pressure around the cutting window is equal to that in the inner cutting cannula; the entire knife set is in an isobaric state; and the sucked and resected tissues are not prone to flowing out from the cutting window to a sample collector, resulting in a problem about a poor sample discharge effect.

SUMMARY OF THE INVENTION

The present invention provides a biopsy rotary cutting device to solve the problem about a poor sample discharge effect.

According to the first aspect of the present invention, a biopsy rotary cutting device is provided, comprising an inner cutting cannula and an outer cutting cannula that are coaxially arranged; the inner cutting cannula is located at the inner side of the outer cutting cannula; the head end of the outer cutting cannula is provided with a piercer; the end of the inner cutting cannula far away from the piercer is directly or indirectly connected with a sample collector; the device also comprises a dynamic sealing structure arranged outside the inner cutting cannula;

the dynamic sealing structure forms a cavity outside the inner cutting cannula; the inner cutting cannula comprises a first tube section and a second tube section that are sequentially arranged along the axial direction of the inner cutting cannula; one end of the first tube section is connected with the piercer; the other end of the first tube section is connected with the second tube section; the outer diameter of the second tube section is smaller than that of the first tube section; a sealing ring is arranged inside the dynamic sealing structure; the cavity comprises a first cavity located at the side of the sealing ring close to the piercer, as well as a second cavity located at the side of the sealing ring far away from the piercer; the first cavity communicates with an inter-cannula gap that is between the outer wall of the first tube section and the inner wall of the outer cutting cannula; and the end of the inter-cannula gap close to the piercer communicates with the inner side space of the inner cutting cannula;

when the inner cutting cannula moves to a first position along its axial direction, the sealing ring is located at the outer side of the second tube section, and there is an inter-cavity gap between the sealing ring and the second tube section to enable the first cavity to communicate with the second cavity;

when the inner cutting cannula moves to a second position along its axial direction, the sealing ring is located at the outer side of the first tube section, and the sealing ring is in sealed contact with the first tube section to isolate the first cavity from the second cavity.

Optionally, the end of the first tube section close to the piercer is provided with a sharp ended structure; a tube wall portion of the outer cutting cannula close to the piercer is provided with a cutting window; the end of the inner cutting cannula far away from the piercer is directly or indirectly connected with the sample collector;

when the inner cutting cannula moves to the first position along its axial direction, the sharp ended structure is located inside the cutting window; and when the inner cutting cannula moves to the second position along its axial direction, the sharp ended structure is not located at the inner side of the cutting window.

Optionally, the device further comprises vent slits that are arranged along the axial direction of the inner cutting cannula; the vent slits are arranged at the sharp ended structure or at the sharp ended structure and the first tube section; the vent slits communicate with the inner side space of the sharp ended structure and the inter-cannula gap; and the inner side space of the sharp ended structure communicates with the inner side space of the first tube section.

Optionally, there are a plurality of vent slits that are uniformly distributed around the axial direction of the inner cutting cannula.

Optionally, each vent slit comprises a main slit portion arranged along the axial direction of the inner cutting cannula, as well as round ends that are respectively arranged at the two ends of the main slit portion.

Optionally, the sharp ended structure comprises a ring-shaped sharp ended connecting portion and a inner cannula tip; the inner cannula tip is arranged at the end of the sharp ended connecting portion close to the piercer; and the end of the sharp ended connecting portion far away from the piercer is connected with the end of the first tube section close to the piercer.

Optionally, the outer diameter of the sharp ended connecting portion is larger than that of the first tube section and smaller than that of the outer cutting cannula.

Optionally, the diameter of the proximal end of the inner cannula tip close to the piercer is larger than the inner diameter of the outer cutting cannula.

Optionally, the dynamic sealing structure comprises a sealing base and a sealing sleeve; the sealing base is fixedly connected to the outside of the outer cutting cannula; the sealing sleeve is fixedly connected with the sealing base; the sealing sleeve and the sealing base have a mounting gap along the axial direction of the inner cutting cannula; the sealing ring is mounted in the mounting gap; the sealing sleeve is located at the outer side of the inner cutting cannula; the first cavity is located inside the sealing base; and the second cavity is located inside the sealing sleeve.

Optionally, the sealing sleeve comprises a sleeve body and a sleeve connecting portion; the sleeve connecting portion is arranged at the side of the sleeve body close to the piercer; the inner side of the sleeve connecting portion is fixedly connected with the outer side of the sealing base; the sleeve body and the sealing base are arranged in a spaced manner along the axial direction of the inner cutting cannula to form the mounting gap.

According to the biopsy rotary cutting device provided by the present invention, in view of the poor sample discharge effect, it is found that the isobaric state can be broken by introducing the atmosphere from the outside, so that the tissues can be sucked out efficiently, wherein by virtue of the dynamic sealing structure and the sealing ring therein, the present invention provides a first cavity that can communicate with an inter-cannula gap between the inner and outer tubes, as well as a second cavity that can communicate with the external atmosphere; during rotary cutting, when the inner cutting cannula moves to the second position, the first cavity and the second cavity are sealed by the sealing ring; the tissues can be sucked into the cutting window under a sealing condition; after rotary cutting, the pressure around the cutting window is equivalent to the pressure generated in the inner cutting cannula; when the inner cutting cannula moves to the first position, the first cavity and the second cavity communicate with each other through the inter-cavity gap outside the second tube section; the atmosphere can be introduced to form a circulating air flow with better suction strength; the circulating air flow passes through the second cavity, the inter-cavity gap, the first cavity and the inter-cannula gap in sequence and enters the inner cutting cannula through the end of the inter-cannula gap close to the piercer; and the circulating air flow can more efficiently send the rotary-cut tissues to the sample collector at the back end, thereby effectively improving the sample discharge rate.

Meanwhile, the first cavity and the second cavity of the present invention are distributed along the axial direction of the inner cutting cannula; the inter-cavity gap is also arranged between the first cavity and the second cavity along the axial direction of the inner cutting cannula; therefore, the overall flow direction of the air flow generated is also along the axial direction, situations such as relatively obvious bending will not occur, thereby not only maintaining relatively high consistency of the flow direction, but also preventing increase of the air flow route, so that the tissue conveying efficiency can be further improved, and increment of the sample discharge rate is facilitated.

In the present invention, the communication and isolation between the first cavity and the second cavity are brought by the movement of the inner cutting cannula; during this period, other human-based or machine-based manipulations are not needed; on the one hand, it can ensure timely communication and isolation; and on the other hand, it can also reduce adverse effects such as resistance caused by communication and isolation on the movement of the inner knife tube.

In addition, as the present invention does not need to introduce other human-based or machine-based manipulations, the present invention can also avoid structural wear degree caused by other manipulations, that is, the present invention can be helpful to reduce wear, to slow down the aging speed and to prolong the service life, thereby facilitating reduction of the maintenance cost.

Meanwhile, as the present invention does not need to introduce other mechanical structures such as reset components, drive components and the like for manipulation, it can also effectively ensure the tightness between the dynamic sealing structure, the cutting cannulas, etc., so as to meet the requirements of high-speed movement in the rotary cutting process (because the rotating speed of a rotary cutting knife is quite high, for example, the rotating speed r can be as high as 300 rpm per second).

DESCRIPTION OF THE DRAWINGS

In order to explain the embodiments of the present invention or the technical schemes in the prior art more clearly, the drawings to be used in the description of the embodiments or the prior art will be briefly introduced as follows; obviously, the drawings described below are only some embodiments of the present invention; for those of ordinary skill in the art, other drawings can be obtained based on these drawings without creative work.

DESCRIPTION OF REFERENCE NUMERALS

1—piercer;
2—outer cutting cannula;
21—cutting window;
3—inner cutting cannula;
31—first tube section;
32—second tube section;
33—sharp ended structure;
331—sharp ended connection portion;
332—inner cannula tip;
333—proximal end;

334—outer bevel;
335—inner bevel;
34—vent slit;
341—main slit portion;
342—round end;
4—dynamic sealing structure;
41—first cavity;
42—second cavity;
43—sealing ring;
44—sealing base;
45—sealing sleeve;
451—sleeve connecting portion;
452—sleeve body;
46—inter-cavity gap;
5—inter-cannula gap;
6—back-end space;
7—dial structure;
71—dial body;
72—dial base;
8—seat rear sleeve.

DETAILED DESCRIPTION

The technical schemes in the embodiments of the present invention will be clearly and completely described below in conjunction with the drawings in the embodiments of the present invention. Obviously, the described embodiments are only a part of the embodiments of the present invention rather than all the embodiments. Based on the embodiments of the present invention, all other embodiments obtained by those of ordinary skill in the art without creative work shall fall within the protection scope of the present invention.

The terms "first", "second", "third", "fourth", etc. (if existing) in the description, claims and the above-mentioned drawings of the present invention are used for distinguishing similar objects rather than describing a specific sequence or order. It should be understood that the data used in this way can be interchanged under appropriate circumstances so that the embodiments of the present invention described herein can be implemented in an order other than those illustrated or described herein. In addition, the terms "include" and "comprise" and any variations of them are intended to cover non-exclusive inclusions; for example, a process, a method, a system, a product or a device that includes a series of steps or units is not necessarily limited to the clearly listed steps or units but can include other unclearly listed steps or units that are inherent to these process, method, product, or equipment.

The technical schemes of the present invention will be described in detail below with specific embodiments. The following specific embodiments can be combined with each other, and the same or similar concepts or processes may not be repeated in some embodiments.

Figure 1:
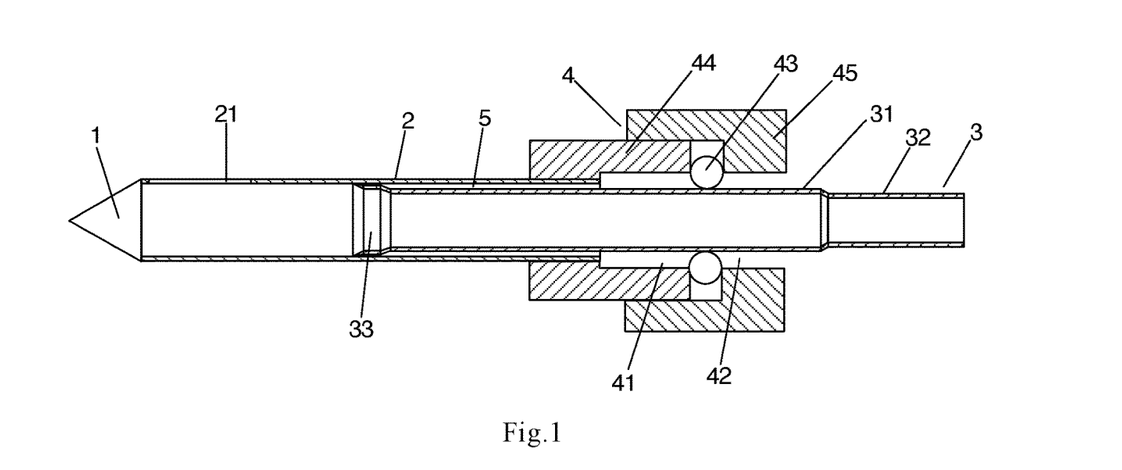
FIG. 1 is a schematic diagram I of the state of the biopsy rotary cutting device in one embodiment of the present invention.
Figure 2:
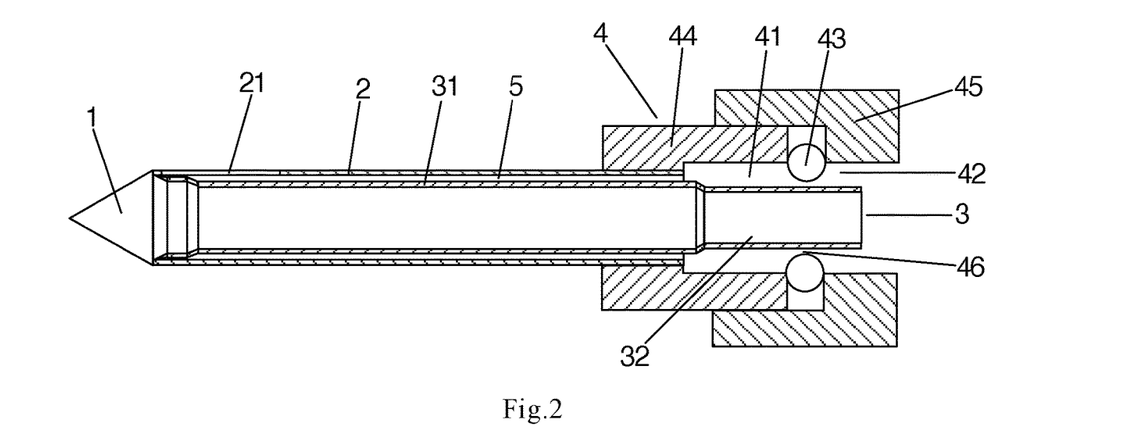
FIG. 2 is a schematic diagram II of the state of the biopsy rotary cutting device in one embodiment of the present invention.

FIG. 1 is the schematic diagram I of the state of the biopsy rotary cutting device in one embodiment of the present invention; and FIG. 2 is the schematic diagram II of the state of the biopsy rotary cutting device in one embodiment of the present invention.

With reference to FIG. 1 and FIG. 2, the biopsy rotary cutting device comprises an inner cutting cannula 3 and an outer cutting cannula 2 that are coaxially arranged; the inner cutting cannula 3 is located at the inner side of the outer cutting cannula 2; the head end of the outer cutting cannula 2 is provided with a piercer 1; the end of the inner cutting cannula 3 far away from the piercer 1 is directly or indirectly connected with a sample collector; and the direct or indirect connection can be understood as that the tissues in the inner cutting cannula 3 can be conveyed to the sample collector.

The tube wall portion of the outer cutting cannula 2 close to the piercer 1 is provided with a cutting window 21; correspondingly, the end of the inner cutting cannula 3 close to the piercer comprises a sharp ended structure 33; the cutting window 21 is used to suck tumor tissues into outer cutting cannula 2; thus, the tissues sucked into the cutting window 21 can be cut by the sharp ended structure 33; the cut tissues are not prone to moving due to equivalent internal and external pressure of the cutting window 21; and the end of the inner cutting cannula 3 far away from the piercer 1 is directly or indirectly connected with the sample collector. The sample collector can be equipped with an externally connected vacuum system. In some schemes, the internal and external pressure difference can be changed by increasing the intensity of the vacuum of the vacuum system.

In this embodiment, the device further comprises a dynamic sealing structure 4 arranged outside the inner cutting cannula 3; the dynamic sealing structure 4 forms a cavity outside the inner cutting cannula 3; the inner cutting cannula 3 comprises a first tube section 31 and a second tube section 32; the end of the second tube section 32 close to the piercer is arranged at the end of the first tube section far away from the piercer, that is, the inner cutting cannula 3 comprises the first tube section 31 and the second tube section 32 that are sequentially arranged along the axial direction of the inner cutting cannula 3; one end of the first tube section 31 is connected with the piercer 1; the other end of the first tube section 31 is connected with the second tube section 32; the outer diameter of the second tube section 32 is smaller than that of the first tube section 31; a sealing ring 43 is arranged inside the dynamic sealing structure 4; the cavity comprises a first cavity 41 located at the side of the sealing ring close to the piercer 1, as well as a second cavity 42 located at the side of the sealing ring 43 far away from the piercer 1; the first cavity 41 communicates with an inter-cannula gap 5 that is between the outer wall of the first tube section 31 and the inner wall of the outer cutting cannula 2; and the end of the inter-cannula gap 5 close to the piercer 1 communicates with the inner side space of the inner cutting cannula 3.

Wherein, the end of the inter-cannula gap 5 close to the piercer 1 can also be understood as close to the cutting window 21, thus when the atmosphere is introduced, the air flow generated by the atmosphere can act on the tissues located close to the cutting window 21 more effectively.

When the inner cutting cannula 3 moves to the first position along its axial direction, the sealing ring 43 is located at the outer side of the second tube section 32, and there is an inter-cavity gap 46 between the sealing ring 43 and the second tube section 32 to enable the first cavity 41 to communicate with the second cavity 42.

When the inner cutting cannula 3 moves to the second position along its axial direction, the sealing ring 43 is located at the outer side of the first tube section 31, and the sealing ring 43 is in sealed contact with the first tube section 31 to isolate the first cavity 41 from the second cavity 42.

The first cavity 41 and the second cavity 42 can be understood as annular cavities that are arranged around the inner cutting cannula 3 and are distributed in sequence along the axial direction of the inner cutting cannula 3; the first cavity 41 may be a cavity communicating with the inter-cannula gap 5; the second cavity 42 may be a cavity that indirectly or directly communicates with the external atmosphere; for example, the second cavity 42 communicates with the external atmosphere through a back-end space 6;

and thus the external atmosphere can be introduced when the first cavity 41 communicates with the second cavity 42.

The first position can be understood as any position that enables the inter-cavity gap 46 to communicate with the first cavity 41 and the second cavity 42, and specifically, it can be the position where the sharp ended structure 33 is located inside the cutting window 21 of the outer cutting cannula 2, namely the sharp ended structure 33 is located inside the cutting window 21 when the inner cutting cannula 3 moves to the first position along its axial direction.

The second position can be understood as any position that enables the inter-cavity gap 46 to isolate the first cavity 41 from the second cavity 42, and specifically, it can be the position where the sharp ended structure 33 is not located inside the cutting window 21 of the outer cutting cannula 2, namely the sharp ended structure 33 is not located inside the cutting window 21 when the inner cutting cannula 3 moves to the second position along its axial direction. At this moment, the vacuum provided by the system is sufficient to allow the tissues to flow into the cutting window 21.

The sharp ended structure 33 may be arranged at the end of the first tube section 31 close to the piercer 1.

According to the biopsy rotary cutting device provided by this embodiment, in view of the poor sample discharge effect, it is found that the isobaric state can be broken by introducing the atmosphere from the outside, so that the tissues can be sucked out efficiently, wherein by virtue of the dynamic sealing structure and the sealing ring therein, the present invention provides a first cavity that can communicate with the inter-cannula gap between the inner and outer tubes, as well as a second cavity that can communicate with the external atmosphere; during rotary cutting, when the inner cutting cannula moves to the second position, the first cavity and the second cavity are sealed by the sealing ring, and the tissues can be sucked into the cutting window under a sealing condition; after rotary cutting, the pressure around the cutting window is equivalent to the pressure generated in the inner cutting cannula; when the inner cutting cannula moves to the first position, the first cavity and the second cavity communicate with each other through the inter-cavity gap outside the second tube section; the atmosphere can be introduced to form a circulating air flow with better suction strength; the circulating air flow passes through the second cavity, the inter-cavity gap, the first cavity and the inter-cannula gap in sequence and enters the inner cutting cannula through the end of the inter-cannula gap close to the piercer; and the circulating air flow can more efficiently send the rotary-cut tissues to the sample collector at the back end, thereby effectively improving the sample discharge rate.

Meanwhile, the first cavity and the second cavity of this embodiment are distributed along the axial direction of the inner cutting cannula; the inter-cavity gap is also arranged between the first cavity and the second cavity along the axial direction of the inner cutting cannula; therefore, the overall flow direction of the air flow generated is also along the axial direction, situations such as relatively obvious bending will not occur, thereby not only maintaining relatively high consistency of the flow direction, but also preventing increase of the air flow route, so that the tissue conveying efficiency can be further improved, and increment of the sample discharge rate is facilitated.

In this embodiment, the communication and isolation between the first cavity and the second cavity are brought by the movement of the inner cutting cannula; during this period, other human-based or machine-based manipulations are not needed; on the one hand, it can ensure timely communication and isolation; and on the other hand, it can also reduce adverse effects such as resistance caused by communication and isolation on the movement of the inner cutting cannula.

In addition, as this embodiment does not need to introduce other human-based or machine-based manipulations, this embodiment can also avoid structural wear degree caused by other manipulations, that is, the present invention can be helpful to reduce wear, to slow down the aging speed and to prolong the service life, thereby facilitating reduction of the maintenance cost. Meanwhile, as this embodiment does not need to introduce other mechanical structures such as reset components, drive components and the like for manipulation, it can also effectively ensure the tightness between the dynamic sealing structure, the cutting cannulas, etc., so as to meet the requirements of high-speed movement in the rotary cutting process (because the rotating speed of a rotary cutting knife is quite high, for example, the rotating speed r can be as high as 300 rpm per second).

Figure 3:
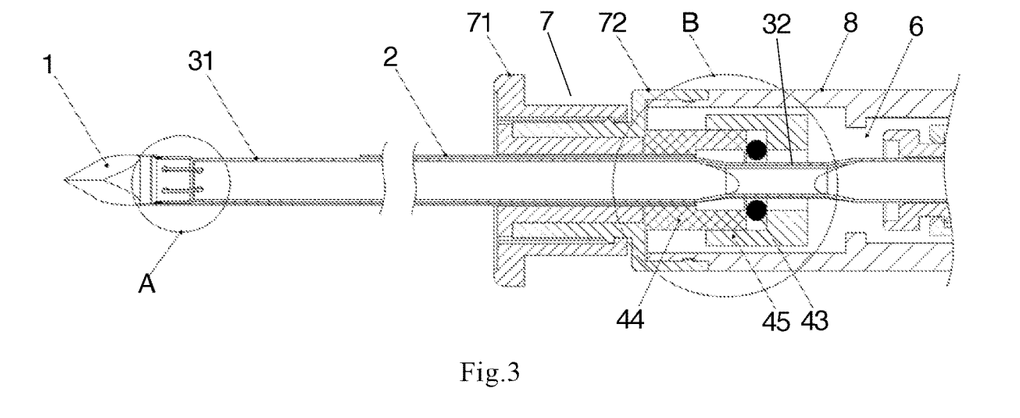
FIG. 3 is a schematic diagram I of the state of the biopsy rotary cutting device in another embodiment of the present invention.
Figure 4:
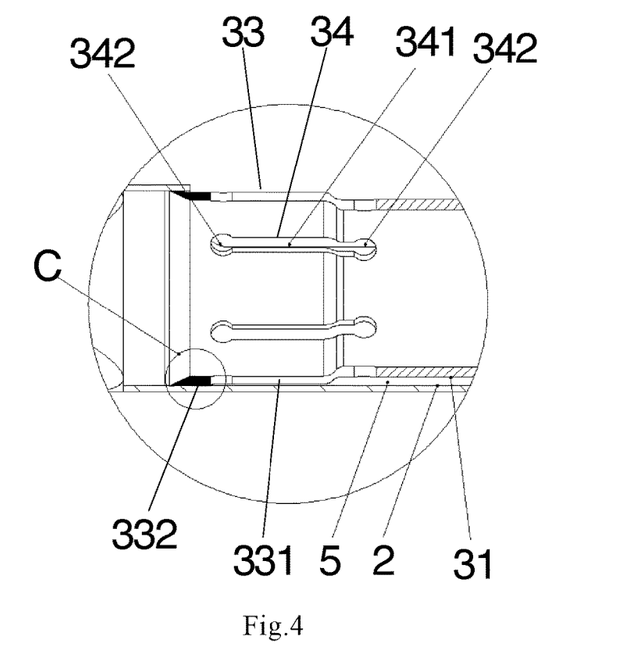
FIG. 4 is a partially enlarged schematic diagram of area A in FIG. 3.
Figure 5:
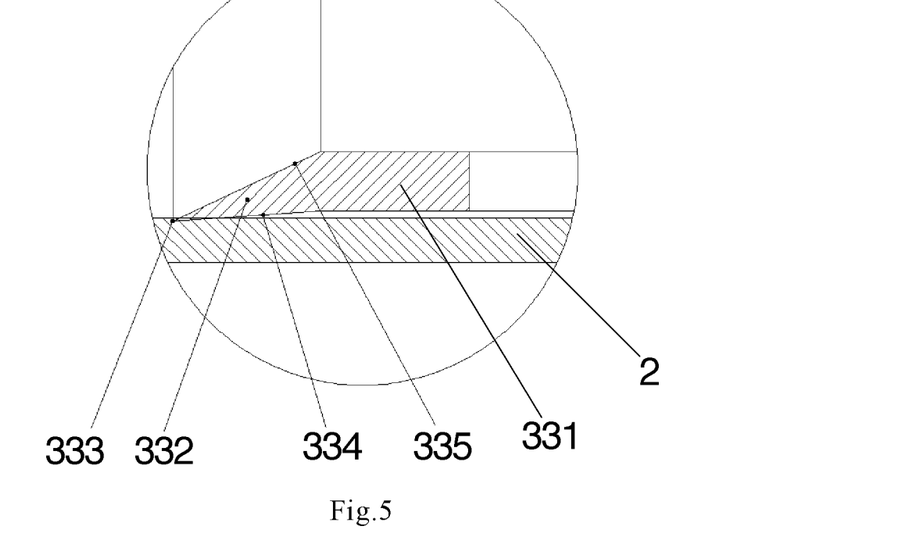
FIG. 5 is a partially enlarged schematic diagram of area C in FIG. 4.
Figure 6:
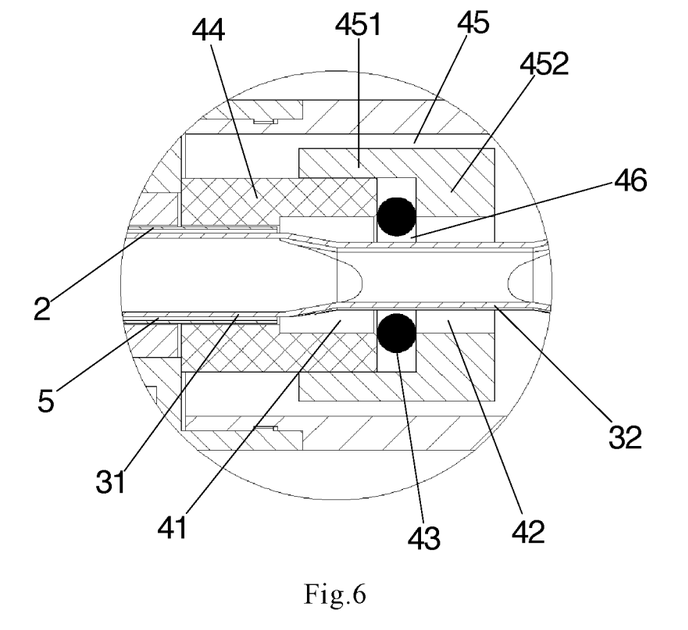
FIG. 6 is a partially enlarged schematic diagram of area B in FIG. 3.
Figure 7:
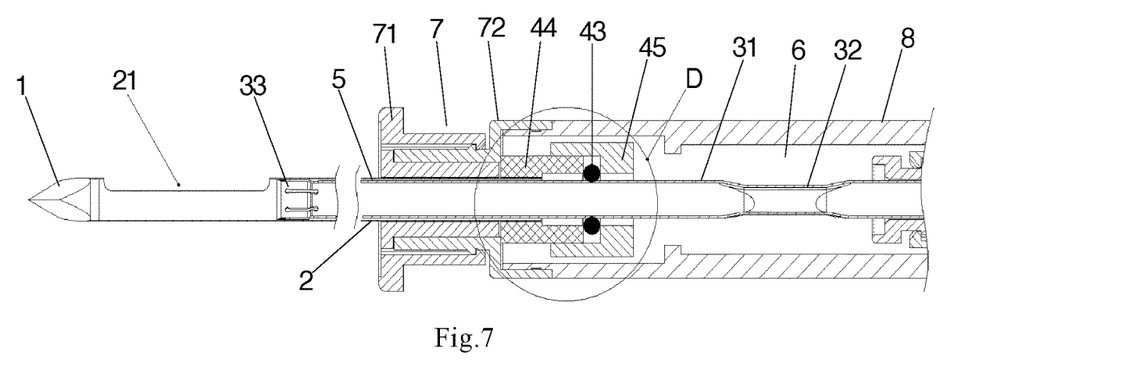
FIG. 7 is a schematic diagram II of the state of the biopsy rotary cutting device in another embodiment of the present invention.

FIG. 3 is a schematic diagram I of the state of the biopsy rotary cutting device in another embodiment of the present invention; FIG. 4 is a partially enlarged schematic diagram of area A in FIG. 3; FIG. 5 is a partially enlarged schematic diagram of area C in FIG. 4; FIG. 6 is a partially enlarged schematic diagram of area B in FIG. 3; FIG. 7 is a schematic diagram II of the state of the biopsy rotary cutting device in another embodiment of the present invention; and FIG. 8 is a partially enlarged schematic diagram of area D in FIG. 7.

In this embodiment, please refer to FIG. 1, FIG. 2, FIG. 3, FIG. 6, FIG. 7 and FIG. 8, the inner cutting cannula 3 rotates forward to the farthest end position, namely the farthest end shown in FIG. 1, FIG. 2, FIG. 3 and FIG. 7; at the moment, the cutting window 21 of the outer cutting cannula 2 is occupied by the distal end of the inner cutting cannula 3, for example, the part including the sharp ended structure 33; this situation can be understood as a penetrating stage, specifically it can be understood with reference to the positions shown in FIG. 2 and FIG. 3, or be understood as the first position.

Figure 8:
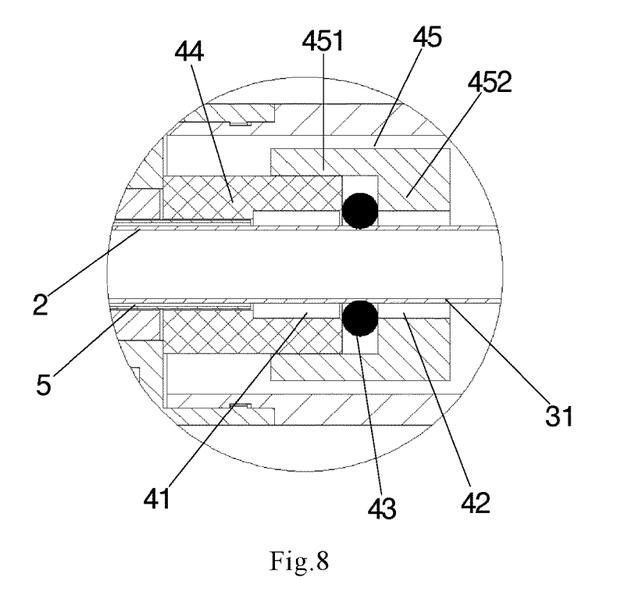
FIG. 8 is a partially enlarged schematic diagram of area D in FIG. 7.

After the penetrating is completed, the inner cutting cannula 3 returns to the position shown in FIG. 1, FIG. 7 and FIG. 8, it can also be understood as returning to the second position; at this moment, for example, the distal end of the sharp ended structure 33 just does not shield the cutting window 21, which is just the stage of tissue suction after the penetrating is completed; at this moment, the first cavity 41 and the second cavity 42 are isolated; the first cavity 41, the inter-cannula gap 5, the inner side space of the sharp ended structure 33 and the inner side space of the first tube section 31 communicate with one another in sequence and are hermetically isolated from the second cavity 42; the tissues can be sucked into the cutting window 21 by utilizing the vacuum system; after the tissues are sucked into the cutting window 21, the inner cutting cannula 3 repeats the action of rotating forward to reach the position shown in FIG. 2 and FIG. 3, that is, the inner cutting cannula 3 rotates to the first position again; and during this process, the sucked tissues are resected by the sharp ended structure 33.

As the inner cutting cannula 3 moves forward, the sealing ring 43 reaches the outer side of the second tube section 32 again to form the inter-cavity gap 46; at this moment, the atmosphere passes through the second cavity 42, the inter-cavity gap 46, the first cavity 41, the inter-cannula gap 5, the inner side space of the sharp ended structure 33 and the inner side space of the first tube section 31 in sequence to form a circulating air flow with better suction strength, thus the tissues are transferred to the sample collector by the continuous vacuum and the introduced atmosphere, thereby completing one time of collection of the tissues.

Wherein, after suction and rotary cutting is completed once, the pressure around the cutting window is equal to the pressure inside the inner cutting cannula 3 and is also equal to the vacuum of the system; when there is no additional atmosphere flowing into the cutting window 21 from the outside, the overall knife set is in an isobaric state, and the sucked and resected tissues cannot or hardly flow from the cutting window 21 to the sample collector. Therefore, this implementation mode effectively realizes the outflow of the tissues by introducing the atmosphere.

It can be seen that the above process completes a cycle of penetrating, suction, rotary cutting and collection, and subsequently the inner cutting cannula 3 can repeat a part or all of the movement of the previous cycle many times until all the tissues to be resected are completely resected.

Wherein, in order to realize the communication between the inner side space of the sharp ended structure 33 and the inter-cannula gap 5, in an optional scheme of this embodiment, different modes for communication between the inter-cannula gap 5 and the inner side space of the inner cutting cannula 3 can be realized according to different structures of the inter-cannula gap 5 at one end of the first tube section 31.

In one of the implementation modes, an interval may be between the periphery of the sharp ended structure 33 and the inner wall of the outer cutting cannula 2, thus the inter-cannula gap 5 can communicate with a space at the side of the sharp ended structure 33 close to the piercer 1 through the interval, that is, the space inside the outer cutting cannula 2 between the sharp ended structure 33 and the piercer 1 thereby communicates with the inner side space of the sharp ended structure 33. In other optional implementation modes, the periphery of the sharp ended structure 33 may also have no interval or a relatively small interval, and meanwhile no interval may further be a structure form that does not hinder the movement of the inner cutting cannula 3 inside the outer cutting cannula 2.

With reference to FIG. 4 and in conjunction with other drawings, the inter-cannula gap 5 can communicate with the inner side of the sharp ended structure 33 through vent slits 34 that are arranged in the sharp ended structure 33. It can be understood as that the device may further comprise vent slits 34 that are arranged along the axial direction of the inner cutting cannula 3; the vent slits 34 are arranged in the sharp ended structure 33 or arranged in the sharp ended structure 33 and the first tube section 31; the vent slits 34 communicate with the inner side space of the sharp ended structure 33 and the inter-cannula gap 5; and the inner side space of the sharp ended structure 33 communicates with the inner side space of the first tube section 31.

The arrangement of the vent slits 34 can ensure that no matter whether or not the inter-cannula gap 5 can communicate with the space at the side of the sharp ended structure 33 close to the piercer 1 through the interval outside the sharp ended structure 33, this implementation mode can realize that the end the inter-cannula gap 5 close to the piercer 1 can communicate with the inner side space of the inner cutting cannula 3, thereby meeting the demands of tissue suction and tissue collection through the circulating air flow.

In one of the implementation modes, with reference to FIG. 4 and FIG. 5, the sharp ended structure 33 comprises a ring-shaped sharp ended connecting portion 331 and a inner cannula tip 332; the inner cannula tip 332 is arranged at the end of the sharp ended connecting portion 331 close to the piercer 1; and the end of the sharp ended connecting portion 331 far away from the piercer 1 is connected with the end of the first tube section 31 close to the piercer 1. Thus, the inner cannula tip 332 may have an outer bevel 334 and an inner bevel 335, and the outer bevel 334 and the inner bevel 335 may be connected to form the proximal end 333 of the inner cannula tip 332.

Wherein, the outer diameter of the sharp ended connecting portion 331 is larger than that of the first tube section 31 and smaller than that of the outer cutting cannula 2, and the diameter of the proximal end 333 of the inner cannula tip 332 close to the piercer 1 may be larger than the inner diameter of the outer cutting cannula 2. In a specific implementation process, the inner diameter of the sharp ended connecting portion 331 may also be larger than the inner diameter of the first tube section 31.

In one of the implementation modes, with reference to FIG. 4, each vent slit 34 comprises a main slit portion 341 arranged along the axial direction of the inner cutting cannula 3, as well as round ends 342 that are respectively arranged at the two ends of the main slit portion 341, thus one round end 342 can be arranged at the sharp ended connecting portion 331, and the other round end 342 can be arranged at the first tube section 31. It can ensure that no matter what angle an inner knife rotates to, the atmosphere can flow from the round ends 342 into the inner side space of the sharp ended structure 33.

Wherein, the diameter of the round ends 342 is larger than the width of the main slit portions 341.

Figure 9:
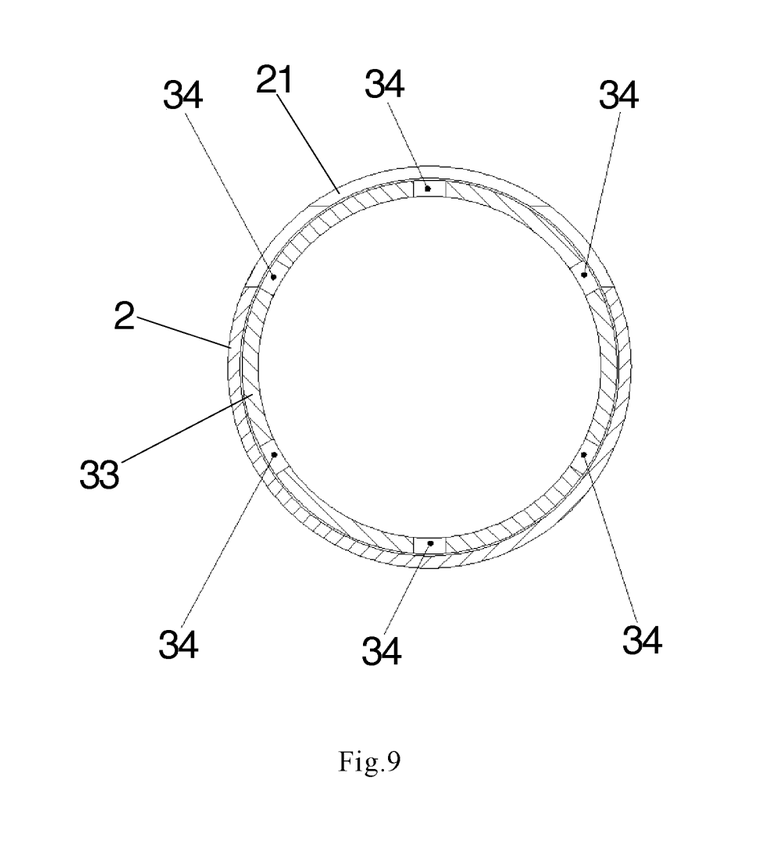
FIG. 9 is a schematic diagram of the distribution of the vent slits in one embodiment of the present invention.

FIG. 9 is a schematic diagram of the distribution of the vent slits in one embodiment of the present invention.

In one of the implementation modes, with reference to FIG. 9, there may be a plurality of vent slits 34 that are uniformly distributed around the axial direction of the inner cutting cannula 3. Further, the circumferential distance between two adjacent vent slits 34 is smaller than the circumferential size of the cutting window 21. As shown in FIG. 9, for example, 6 vent slits 34 can be set to be uniformly distributed along the circumference to ensure that no matter what angle the inner cutting cannula rotates to, there are vent slits 34 located inside the cutting window 21 of the outer cutting cannula 2, and thus the generated air flow can flow near the cutting window 21.

In one of the implementation modes, the dynamic sealing structure 4 comprises a sealing base 44 and a sealing sleeve 45; the sealing base 44 is fixedly connected to the outside of the outer cutting cannula 2 directly or indirectly; the sealing sleeve 45 is fixedly connected with the sealing base 44; the sealing sleeve 45 and the sealing base 44 have a mounting gap along the axial direction of the inner cutting cannula 3; the sealing ring 43 is mounted in the mounting gap; the sealing sleeve 45 is located at the outer side of the inner cutting cannula 3; the first cavity 41 is located inside the sealing base 44; and the second cavity 42 is located inside the sealing sleeve 45.

Wherein, the sealing base 44 can be fixedly connected with a dial structure 7; for example, the head end surface of the sealing base 44 and the inner end surface of a dial base 72 in the dial structure 7 can be connected and completely sealed; and the connection way is not limited to glue adhesion, laser welding, etc. There is a certain gap between the head end surface of the sealing base 44 and the inner end surface of a dial body 71 in the dial structure 7 to ensure that the dial body 71 can rotate about the axis of the outer cutting cannula 2.

In a further optional implementation mode, or in other optional implementation modes, the outer surface of the outer cutting cannula 2 may also be fixedly connected with the inner surface of the sealing base 44, and the fixation way is not limited to glue adhesion, laser welding, etc.

In a specific implementation process, with reference to FIG. 6 and FIG. 7, the sealing sleeve 45 comprises a sleeve body 452 and a sleeve connecting portion 451; the sleeve connecting portion 451 is arranged at the side of the sleeve body 452 close to the piercer 1; the inner side of the sleeve connecting portion 451 is fixedly connected with the outer side of the sealing base 44; and the sleeve body 452 and the sealing base 44 are arranged in a spaced manner along the axial direction of the inner cutting cannula 3 to form the mounting gap. The size of the mounting gap can be matched with the size of the sealing ring 43, so as to be suitable for realizing the installation of the sealing ring 43.

The connection and fixation way between the outer surface of the sealing base 44 and the inner surface of the sealing sleeve 45 may be various, and are not limited to glue adhesion, screw thread fit, etc.

In other optional implementation modes, the sealing sleeve 45 and the sealing base 44 can also be integrally formed, thus the mounting gap can be formed randomly, and all integrated or assembled dynamic sealing structures 4 that can be directly or indirectly connected with the outer cutting cannula 2 do not deviate from the description scope of this embodiment.

In addition, the side of the dial structure 7 far away from the piercer 1 is connected with a seat rear sleeve 8; the back-end space 6 can be located inside the seat rear sleeve 8; the sealing sleeve 45 can also be located at the inner side of the seat rear sleeve 8; and the sealing base 44 can be located at the inner side of the dial base 72 of the dial structure 7.

In conclusion, according to the biopsy rotary cutting device provided by this embodiment, in view of the situation about the poor sample discharge effect, it is found that the isobaric state can be broken by introducing the atmosphere from the outside, so that the tissues can be sucked out efficiently, wherein by virtue of the dynamic sealing structure and the sealing ring therein, the present invention provides a first cavity that can communicate with the inter-cannula gap between the inner and outer tubes, as well as a second cavity that can communicate with the external atmosphere; during rotary cutting, when the inner cutting cannula moves to the second position, the first cavity and the second cavity are sealed by the sealing ring, and the tissues can be sucked into the cutting window under a sealing condition; after rotary cutting, the pressure around the cutting window is equivalent to the pressure generated in the inner cutting cannula; when the inner cutting cannula moves to the first position, the first cavity and the second cavity communicate with each other through the inter-cavity gap outside the second tube section; the atmosphere can be introduced to form a circulating air flow with better suction strength; the circulating air flow passes through the second cavity, the inter-cavity gap, the first cavity and the inter-cannula gap in sequence and enters the inner cutting cannula through the end of the inter-cannula gap close to the piercer; and the circulating air flow can more efficiently send the rotary-cut tissues to the sample collector at the back end, thereby effectively improving the sample discharge rate.

Meanwhile, the first cavity and the second cavity of this embodiment are distributed along the axial direction of the inner cutting cannula; the inter-cavity gap is also arranged between the first cavity and the second cavity along the axial direction of the inner cutting cannula; therefore, the overall flow direction of the air flow generated is also along the axial direction, situations such as relatively obvious bending will not occur, thereby not only maintaining relatively high consistency of the flow direction, but also preventing increase of the air flow route, so that the tissue conveying efficiency can be further improved, and increment of the sample discharge rate is facilitated.

In this embodiment, the communication and isolation between the first cavity and the second cavity are brought by the movement of the inner cutting cannula; during this period, other human-based or machine-based manipulations are not needed; on the one hand, it can ensure timely communication and isolation; and on the other hand, it can also reduce adverse effects such as resistance caused by communication and isolation on the movement of the inner cutting cannula.

In addition, as this embodiment does not need to introduce other human-based or machine-based manipulations, this embodiment can also avoid structural wear degree caused by other manipulations, that is, the present invention can be helpful to reduce wear, to slow down the aging speed and to prolong the service life, thereby facilitating reduction of the maintenance cost. Meanwhile, as the present invention does not need to introduce other mechanical structures such as reset components, drive components and the like for manipulation, it can also effectively ensure the tightness between the dynamic sealing structure, the cutting cannulas, etc., so as to meet the requirements of high-speed movement in the rotary cutting process (because the rotating speed of a rotary cutting knife is quite high, for example, the rotating speed r can be as high as 300 rpm per second).

Finally, it should be noted that all the above embodiments are only used to illustrate the technical schemes of the present invention, but not to limit them; although the present invention has been described in detail with reference to all the aforementioned embodiments, those of ordinary skill in the art should understand: the technical schemes recorded in the aforementioned embodiments can still be modified, or some or all of the technical features can be equivalently replaced; these modifications or replacements do not make the essence of the corresponding technical schemes deviate from the scope of the technical schemes of all the embodiments of the present invention.

The invention claimed is:

1. A biopsy rotary cutting device, comprising:
   an inner cutting cannula and an outer cutting cannula that are coaxially arranged, wherein the inner cutting cannula is located at an inner side of the outer cutting cannula;
   a piercer arranged at a head end of the outer cutting cannula, wherein a distal end of the inner cutting cannula is directly or indirectly connected with a sample collector;
   a dynamic sealing structure arranged outside the inner cutting cannula, wherein the dynamic sealing structure forms a cavity outside the inner cutting cannula;
   wherein the inner cutting cannula comprises a first tube section and a second tube section that are sequentially arranged along an axial direction of the inner cutting cannula, wherein a first end of the first tube section is connected with the piercer, a second end of the first tube section is connected with the second tube section, an outer diameter of the second tube section is smaller than that of the first tube section;
   a sealing ring arranged inside the dynamic sealing structure;
   wherein the cavity comprises a first cavity located at a first side of the sealing ring proximal to the piercer, as well as a second cavity located at a second side of the sealing ring distal to the piercer;
wherein the first cavity communicates with an inter-cannula gap that is between an outer wall of the first tube section and an inner wall of the outer cutting cannula; and
a first end of the inter-cannula gap proximal to the piercer communicates with an inner side space of the inner cutting cannula;
wherein the inner cutting cannula moves between a first position and a second position along the axial direction,
wherein at the first position, the sealing ring surrounds the second tube section, and there is an inter-cavity gap between the sealing ring and the second tube section to enable the first cavity to communicate with the second cavity;
and at the second position, the sealing ring surrounds the first tube section, and the sealing ring is in sealed contact with the first tube section to isolate the first cavity from the second cavity.

2. The device according to claim 1, wherein the first end of the first tube section is provided with a sharp ended structure; a tube wall portion of the outer cutting cannula is provided with a cutting window;
when the inner cutting cannula moves to the first position along the axial direction, the sharp ended structure is located inside the cutting window; and when the inner cutting cannula moves to the second position along the axial direction, the sharp ended structure is not located inside the cutting window.

3. The device according to claim 2, characterized by further comprising vent slits arranged along the axial direction of the inner cutting cannula; the vent slits are arranged at the sharp ended structure or at the sharp ended structure and the first tube section; the vent slits communicate with an inner side space of the sharp ended structure and the inter-cannula gap; and the inner side space of the sharp ended structure communicates with the inner side space of the first tube section.

4. The device according to claim 3, wherein there are a plurality of vent slits that are uniformly distributed around the axial direction of the inner cutting cannula.

5. The device according to claim 4, wherein the sharp ended structure comprises a ring-shaped sharp ended connecting portion and an inner cannula tip; the inner cannula tip is arranged at a first end of the sharp ended connecting portion; and a second end of the sharp ended connecting portion is connected with the first end of the first tube section close to the piercer.

6. The device according to claim 4, wherein the dynamic sealing structure comprises a sealing base and a sealing sleeve; the sealing base is fixedly connected to an outer wall of the outer cutting cannula; the sealing sleeve is fixedly connected with the sealing base; the sealing sleeve and the sealing base have a mounting gap along the axial direction of the inner cutting cannula; the sealing ring is mounted in the mounting gap; the sealing sleeve is located at an outer side of the inner cutting cannula; the first cavity is located inside the sealing base; and the second cavity is located inside the sealing sleeve.

7. The device according to claim 6, wherein the sealing sleeve comprises a sleeve body and a sleeve connecting portion; the sleeve connecting portion is arranged at a first side of the sleeve body; an inner side of the sleeve connecting portion is fixedly connected with an outer side of the sealing base; the sleeve body and the sealing base are arranged in a spaced manner along the axial direction of the inner cutting cannula to form the mounting gap.

8. The device according to claim 3, wherein each vent slit comprises a main slit portion arranged along the axial direction of the inner cutting cannula, as well as round ends that are respectively arranged at two ends of the main slit portion.

9. The device according to claim 8, wherein the sharp ended structure comprises a ring-shaped sharp ended connecting portion and an inner cannula tip; the inner cannula tip is arranged at a first end of the sharp ended connecting portion; and a second end of the sharp ended connecting portion is connected with the first end of the first tube section.

10. The device according to claim 8, wherein the dynamic sealing structure comprises a sealing base and a sealing sleeve; the sealing base is fixedly connected to an outer wall of the outer cutting cannula; the sealing sleeve is fixedly connected with the sealing base; the sealing sleeve and the sealing base have a mounting gap along the axial direction of the inner cutting cannula; the sealing ring is mounted in the mounting gap; the sealing sleeve is located at an outer side of the inner cutting cannula; the first cavity is located inside the sealing base; and the second cavity is located inside the sealing sleeve.

11. The device according to claim 10, wherein the sealing sleeve comprises a sleeve body and a sleeve connecting portion; the sleeve connecting portion is arranged at a first side of the sleeve body; an inner side of the sleeve connecting portion is fixedly connected with an outer side of the sealing base; the sleeve body and the sealing base are arranged in a spaced manner along the axial direction of the inner cutting cannula to form the mounting gap.

12. The device according to claim 3, wherein the sharp ended structure comprises a ring-shaped sharp ended connecting portion and an inner cannula tip; the inner cannula tip is arranged at a first end of the sharp ended connecting portion; and a second end of the sharp ended connecting portion is connected with the first end of the first tube section.

13. The device according to claim 12, wherein an outer diameter of the sharp ended connecting portion is larger than that of the first tube section and smaller than that of the outer cutting cannula.

14. The device according to claim 13, wherein an inner diameter of a proximal end of the inner cannula tip is larger than an inner diameter of the outer cutting cannula.

15. The device according to claim 3, wherein the dynamic sealing structure comprises a sealing base and a sealing sleeve; the sealing base is fixedly connected to an outer wall of the outer cutting cannula; the sealing sleeve is fixedly connected with the sealing base; the sealing sleeve and the sealing base have a mounting gap along the axial direction of the inner cutting cannula; the sealing ring is mounted in the mounting gap; the sealing sleeve is located at an outer side of the inner cutting cannula; the first cavity is located inside the sealing base; and the second cavity is located inside the sealing sleeve.

16. The device according to claim 15, wherein the sealing sleeve comprises a sleeve body and a sleeve connecting portion; the sleeve connecting portion is arranged at a first side of the sleeve body; an inner side of the sleeve connecting portion is fixedly connected with an outer side of the sealing base; the sleeve body and the sealing base are arranged in a spaced manner along the axial direction of the inner cutting cannula to form the mounting gap.

17. The device according to claim 2, wherein the dynamic sealing structure comprises a sealing base and a sealing sleeve; the sealing base is fixedly connected to an outer wall of the outer cutting cannula; the sealing sleeve is fixedly connected with the sealing base; the sealing sleeve and the sealing base have a mounting gap along the axial direction of the inner cutting cannula; the sealing ring is mounted in the mounting gap; the sealing sleeve is located at an outer side of the inner cutting cannula; the first cavity is located inside the sealing base; and the second cavity is located inside the sealing sleeve.

18. The device according to claim 17, wherein the sealing sleeve comprises a sleeve body and a sleeve connecting portion; the sleeve connecting portion is arranged at a first side of the sleeve body; an inner side of the sleeve connecting portion is fixedly connected with an outer side of the sealing base; the sleeve body and the sealing base are arranged in a spaced manner along the axial direction of the inner cutting cannula to form the mounting gap.

19. The device according to claim 1, wherein the dynamic sealing structure comprises a sealing base and a sealing sleeve; the sealing base is fixedly connected to an outer wall of the outer cutting cannula; the sealing sleeve is fixedly connected with the sealing base; the sealing sleeve and the sealing base have a mounting gap along the axial direction of the inner cutting cannula; the sealing ring is mounted in the mounting gap; the sealing sleeve is located at an outer side of the inner cutting cannula; the first cavity is located inside the sealing base; and the second cavity is located inside the sealing sleeve.

20. The device according to claim 19, wherein the sealing sleeve comprises a sleeve body and a sleeve connecting portion; the sleeve connecting portion is arranged at a first side of the sleeve body; an inner side of the sleeve connecting portion is fixedly connected with an outer side of the sealing base; the sleeve body and the sealing base are arranged in a spaced manner along the axial direction of the inner cutting cannula to form the mounting gap.

* * * * *